(12) United States Patent
Yamashita et al.

(10) Patent No.: US 9,738,587 B2
(45) Date of Patent: Aug. 22, 2017

(54) METHOD FOR PRODUCING 2-ISOPROPENYL-5-METHYL-4-HEXEN-1-YL 3-METHYL-2-BUTENOATE

(71) Applicant: Shin-Etsu Chemical Co., Ltd., Tokyo (JP)

(72) Inventors: Miyoshi Yamashita, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/950,125

(22) Filed: Nov. 24, 2015

(65) Prior Publication Data
US 2016/0152544 A1 Jun. 2, 2016

(30) Foreign Application Priority Data
Dec. 2, 2014 (JP) .................. 2014-244181

(51) Int. Cl.
*C07C 67/03* (2006.01)
*B01J 31/12* (2006.01)
*B01J 31/14* (2006.01)

(52) U.S. Cl.
CPC .............. *C07C 67/03* (2013.01); *B01J 31/12* (2013.01); *B01J 31/143* (2013.01); *B01J 2231/49* (2013.01)

(58) Field of Classification Search
None
See application file for complete search history.

(56) References Cited

U.S. PATENT DOCUMENTS

| 3,781,333 A | 12/1973 | Kappeler et al. |
| 2009/0023941 A1 | 1/2009 | Ujita et al. |
| 2010/0063314 A1 | 3/2010 | Ujita et al. |

FOREIGN PATENT DOCUMENTS

| EP | 2119693 A1 | 11/2009 |
| JP | 58-148832 | 9/1983 |
| JP | 2002-308815 | 10/2002 |
| WO | WO 2006/109570 A1 | 10/2006 |
| WO | WO 2008/075468 A1 | 6/2008 |

OTHER PUBLICATIONS

Zada et al. Tetrahedron: Asymmetry, 2004, 15(15), 2339-2343.*
Hoydonckx et al. Topics in Catalysis vol. 27, No. 1-4, 2004, 83-96.*
Bristow "Polymerization of Allylic Methacrylates Part 2-Substituted Allyl Methacrylates", *Trans. Faraday Soc.* 54:1064-1068 (1958).
Fleming et al. "Conjugate Addition of Silyl Groups to β-Unsubstituted Enones, & Si-to-OH Conversion: a Synthesis of (±)-Lavandulol", *Tetrahedron Letters* 37(38):6929-6930 (1996).
Hinkens et al, "Identification and synthesis of the sex pheromone of the vine mealybug, Planococcus ficus", *Tetrahedron Letters* 42:1619-1621 (2001).
Otera et al. "Novel Distannoxane-Catalyzed Transesterification and a New Entry to α,β-Unsaturated Carboxylic Acids", *Tetrahedron Letters* 27(21):2383-2386 (1986).
Tolstikov et al. "Synthesis of Analogs of Juvenile Hormone on the Basis of the Telormerization Reaction of Piperylene With Sulfones", *Bulletin of the Academy of Sciences of the USSR, Division of Chemical Sciences* 35(4):795-799 (1986).
Ueno et al. "Synthesis of (±)-Lavandulol and its Related Homoallylic Alcohol via Ally Transfer from Sulphur to Tin", *J. Chem. Soc., Chem. Comm.* pp. 683-384 (1980).
European Search Report corresponding to European Application No. 15197129 dated Apr. 14, 2016.

\* cited by examiner

*Primary Examiner* — Sudhakar Katakam
*Assistant Examiner* — Ana Z Muresan
(74) *Attorney, Agent, or Firm* — Myers Bigel, P.A.

(57) ABSTRACT

Provided is a method for industrially producing 2-isopropenyl-5-methyl-4-hexen-1-yl 3-methyl-2-butenoate, which is, for example, a sex pheromone substance of vine mealybug. More specifically, there is provided a method for producing 2-isopropenyl-5-methyl-4-hexen-1-yl 3-methyl-2-butenoate, comprising a step of transesterifying 2-isopropenyl-5-methyl-4-hexen-1-ol represented by Formula (1) with alkyl senecioate represented by General Formula (2) in the presence of a catalyst, while distilling off an alcohol represented by General Formula (4) formed as a by-product, to obtain 2-isopropenyl-5-methyl-4-hexen-1-yl 3-methyl-2-butenoate represented by Formula (3).

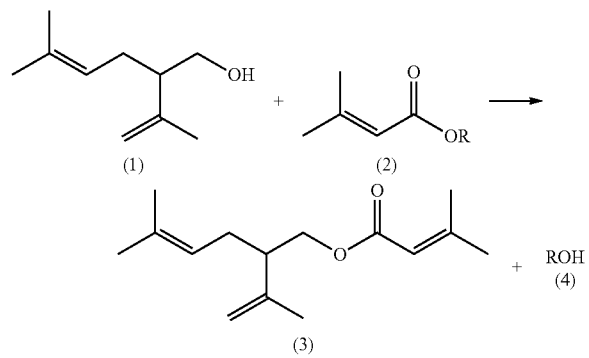

2 Claims, No Drawings

METHOD FOR PRODUCING 2-ISOPROPENYL-5-METHYL-4-HEXEN-1-YL 3-METHYL-2-BUTENOATE

RELATED APPLICATION

This application claims priority from Japanese Patent Application No. 2014-244181, filed Dec. 2, 2014, the disclosure of which is incorporated by reference herein in its entirety.

FIELD AND BACKGROUND OF THE INVENTION

The present invention relates to 2-isopropenyl-5-methyl-4-hexen-1-yl 3-methyl-2-butenoate (generic name: lavandulyl senecioate) as a sex pheromone component of vine mealybug (scientific name: Planococcus ficus).

Vine mealybug (scientific name: Planococcus ficus) is known as one of major insects of grapevines and damages fruits of grapevines, causing serious problems such as reductions in the yield and the crop quality. At the present time, insecticides are used to control the vine mealybug without sufficient success. Because of concerns about the environment and human health affected by the use of insecticides, there is a demand for the development of novel insect pest control methods such as mating disruption and mass trapping by using sex pheromone substances.

The sex pheromone substance that is secreted by females of the vine mealybug and is used for reproductive behavior is 2-isopropenyl-5-methyl-4-hexen-1-yl 3-methyl-2-butenoate (generic name: lavandulyl senecioate), which has been reported by Diane M. Hinkens et al. (Tetrahedron Letters 42 (2001) 1619-1621).

The existing method for producing 2-isopropenyl-5-methyl-4-hexen-1-yl 3-methyl-2-butenoate is exemplified by the method reported by Diane M. Hinkens et al. (Tetrahedron Letters 42 (2001) 1619-1621). In the method, senecioyl halide prepared by halogenation of senecioic acid is reacted with 2-isopropenyl-5-methyl-4-hexen-1-ol in the presence of an organic base. However, when the compound is produced in an industrial scale by the method of Hinkens et al., by-products are formed during the purification by distillation to lower the yield. To address the problem, WO 2008/075468 discloses the method in which an unpurified 2-isopropenyl-5-methyl-4-hexen-1-yl 3-methyl-2-butenoate is heat-treated in the presence of a basic substance and then is purified by distillation.

Another production method is also reported in WO 2006/109570. In the method, a sulfonate ester prepared from 2-isopropenyl-5-methyl-4-hexen-1-ol and an organic sulfonyl halide is reacted with senecioic acid in the presence of a basic substance.

SUMMARY OF THE INVENTION

The production method described in WO 2008/075468 unfortunately requires a plurality of production steps. In addition, after the reaction, the unpurified 2-isopropenyl-5-methyl-4-hexen-1-yl 3-methyl-2-butenoate is required to be heat-treated for a long period of time in the presence of a basic substance such as sodium carbonate, thereby the method requiring a lot of time. The production method described in WO 2006/109570 requires a plurality of production steps, and the reaction is complicated. In addition, a large amount of a solid basic substance such as potassium carbonate or sodium carbonate is used in the reaction of a sulfonate ester compound and senecioic acid, and thus a large amount of a solvent is required in order to maintain stirring of the reaction solution, resulting in a small amount of product per volume of the reactor. It is known that when a sex pheromone substance is mixed with an isomer thereof such as a geometric isomer, a positional isomer and an optical isomer, the activity thereof can be suppressed. In the production method described in WO 2006/109570, the reaction is carried out with heat for a long period of time in the presence of a basic substance, and thus 1.5 to 2.0% of 2-isopropenyl-5-methyl-4-hexen-1-yl 3-methyl-3-butenoate, which is a positional isomer of 2-isopropenyl-5-methyl-4-hexen-1-yl 3-methyl-2-butenoate, is unfortunately produced as a by-product. As described above, in the existing production methods, large amounts of isomers are formed as by-products, and the productivity is low. Such methods have problems for the industrial mass production.

In view of the above circumstances, the present invention has been made to solve the problems in the conventional methods. An object of the present invention is to provide a method for industrially producing 2-isopropenyl-5-methyl-4-hexen-1-yl 3-methyl-2-butenoate, which is, for example, a sex pheromone substance of vine mealybug.

The inventors of the present invention have intensively studied in order to solve the problems, and consequently have found that transesterification of alkyl senecioate (2) in place of senecioyl halide, which is a cause of generating a by-product during distillation, with 2-isopropenyl-5-methyl-4-hexen-1-ol (1) can simply produce 2-isopropenyl-5-methyl-4-hexen-1-yl 3-methyl-2-butenoate at a high yield while production of isomer as a by-product is suppressed and a by-product is not formed during distillation. The reaction can be carried out without a solvent, so that it has been found that the amount of product per volume of the reactor is improved. As a result, the present invention has been completed.

In one aspect of the present invention, there is provided a method for producing 2-isopropenyl-5-methyl-4-hexen-1-yl 3-methyl-2-butenoate, comprising a step of transesterifying 2-isopropenyl-5-methyl-4-hexen-1-ol represented by Formula (1) with alkyl senecioate represented by General Formula (2) in the presence of a catalyst, while distilling off an alcohol represented by General Formula (4) formed as a by-product, to obtain 2-isopropenyl-5-methyl-4-hexen-1-yl 3-methyl-2-butenoate represented by Formula (3).

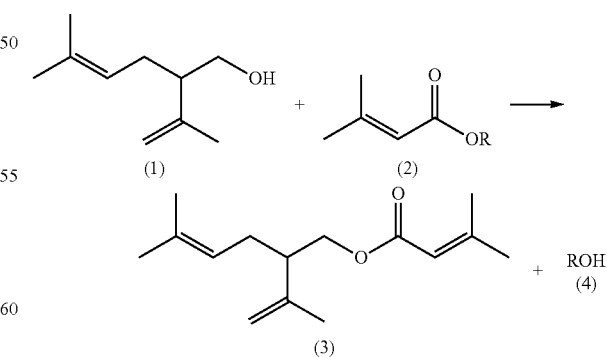

In the above, R is a saturated or unsaturated linear alkyl group having 1 to 6 carbon atoms.

According to the present invention, 2-isopropenyl-5-methyl-4-hexen-1-yl 3-methyl-2-butenoate, which is, for example, a sex pheromone substance of vine mealybug, can be efficiently and industrially produced at low cost.

DETAILED DESCRIPTION OF THE INVENTION

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

2-Isopropenyl-5-methyl-4-hexen-1-ol (1) shown below can be produced by a known method.

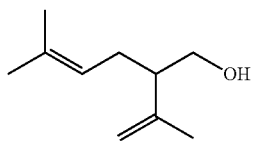

(1)

Examples of the method for producing 2-isopropenyl-5-methyl-4-hexen-1-ol (1) include the method comprising the steps of subjecting isopentenyl bromide and senecioic acid ester to a condensation reaction in sodium amide to obtain an ester, and reducing the ester (Japanese Patent Application Examined Publication No. 39-7756); the method comprising the steps of reacting 2-methyl-2-propenyl tolyl sulfone with isopentenyl bromide to obtain an allyl sulfone compound, reacting the allyl sulfone compound with tributyltin hydride in the presence of azobisisobutyronitrile (AIBN) to obtain a tin compound, and hydroxymethylating the tin compound (Y. Ueno et al., J. Chem. Soc., Chem. Commun., 1980, 683); the method comprising the steps of rearranging 2-methylbuten-2-yl dimethylacrylate with sodium hydride, and reducing the resulting product with lithium aluminum hydride (U.S. Pat. No. 3,781,333); the method comprising the steps of silylating an enone compound, and then subjecting to the Wittig reaction to convert the silyl group into alcohol (I. Fleming et al., Tetrahedron Lett., 37, 38, 6929, 1996); the method comprising the step of rearranging diprenyl ether or 1,1-dimethyl-2-propenyl prenyl ether in the presence of an aluminum compound (Japanese Patent Application Unexamined Publication No. 58-148832); and the method comprising the steps of reacting 3-methyl-2-butenal dimethyl acetal with 3-methyl-1-buten-3-ol in the presence of an acid catalyst to obtain lavandulal, and reducing the lavandulal (Japanese Patent Application Unexamined Publication No. 2002-308815).

The alkyl senecioate (2) shown below is used for transesterification.

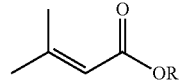

(2)

In the above formula, R represents a saturated or unsaturated linear alkyl group having 1 to 6 carbon atoms.

Specific examples of the alkyl senecioate include saturated alkyl esters of senecioic acid such as methyl senecioate, ethyl senecioate, n-propyl senecioate and n-butyl senecioate; and unsaturated alkyl esters of senecioic acid such as vinyl senecioate and isopropenyl senecioate. Among them, methyl senecioate, ethyl senecioate, vinyl senecioate and isopropenyl senecioate are preferred, and methyl senecioate and ethyl senecioate are particularly preferred from the viewpoint of easy availability and reactivity.

The amount of the alkyl senecioate to be used for the transesterification is preferably 1.0 mol to 3.0 mol relative to 1.0 mol of 2-isopropenyl-5-methyl-4-hexen-1-ol (1), and is particularly preferably 1.2 to 2.0 mol relative to 1.0 mol of 2-isopropenyl-5-methyl-4-hexen-1-ol (1) from the viewpoint of reaction rate and cost efficiency.

By the transesterification, 2-isopropenyl-5-methyl-4-hexen-1-yl 3-methyl-2-butenoate (3) shown below is produced as the target compound, together with the alcohol (4) shown below as a by-product.

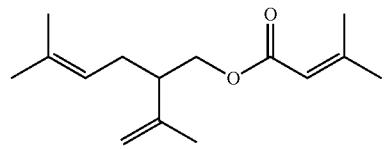

(3)

The alcohol formed as a by-product varies depending on the type of the alkyl senecioate used. Examples of the alcohol include saturated alcohols such as methanol, ethanol, n-propanol and n-butanol; and unsaturated alcohols such as vinyl alcohol and isopropenol. Vinyl alcohol and isopropenol are unstable and immediately converted into acetaldehyde and acetone, respectively. Among them, methanol, ethanol, vinyl alcohol (acetaldehyde after conversion) and isopropenol (acetone after conversion) are preferred, and methanol and ethanol are particularly preferred from the viewpoint of reactivity and separation by distillation.

Examples of the catalyst to be used for the transesterification include an acid such as hydrochloric acid, sulfuric acid, trifluoroacetic acid, methanesulfonic acid, benzenesulfonic acid, p-toluenesulfonic acid and Amberlyst 15; an alkali metal salt of alcohol such as sodium methoxide, sodium ethoxide and potassium t-butoxide; a metal carboxylate such as sodium acetate, potassium acetate, calcium acetate, tin acetate, zinc acetate and aluminum acetate; a Lewis acid containing an aluminum atom, such as aluminum trichloride, chloroaluminum ethoxide, dichloroaluminum ethoxide, aluminum methoxide, aluminum ethoxide and aluminum isopropoxide; a Lewis acid containing a zinc atom, such as zinc chloride and zinc bromide; a Lewis acid containing a boron atom, such as boron trifluoride, boron trichloride and boron tribromide; a Lewis acid containing a tin atom, such as tin tetrachloride, dibutyltin dichloride, dibutyltin dimethoxide, dibutyltin oxide, monobutyltin oxide and dibutyltin dichloride; and a Lewis acid containing a titanium atom, such as titanium tetrachloride, titanium tetrabromide, titanium(IV) methoxide, titanium(IV) ethoxide, titanium(IV) isopropoxide and titanium(IV) oxide. Among them, a Lewis acid containing a titanium atom, a Lewis acid containing a tin atom and a Lewis acid containing an aluminum atom are preferred from the viewpoint of reactivity and a small amount of impurity; and titanium(IV) methoxide, titanium(IV) ethoxide, titanium(IV) isopropoxide, dibutyltin dimethoxide, dibutyltin oxide, dibutyltin dichloride, aluminum methoxide, aluminum ethoxide and aluminum isopropoxide are particularly preferred from the viewpoint of yield and a small amount of impurity.

The amount of the catalyst to be used for the transesterification is preferably 0.001 to 0.5 mol relative to 1.0 mol of 2-isopropenyl-5-methyl-4-hexen-1-ol (1), and is particularly preferably 0.005 to 0.05 mol relative to 1.0 mol of 2-isopropenyl-5-methyl-4-hexen-1-ol (1) from the viewpoint of cost efficiency and yield.

The transesterification can be carried out commonly without a solvent. However, a solvent can be supplementally used to facilitate the removal of the alcohol formed as a by-product. The solvent can be any solvent that does not adversely affect the reaction, and preferred examples of the solvent include a hydrocarbon solvent such as hexane, benzene, toluene and xylene; and an ether solvent such as tetrahydrofuran, di-n-butyl ether, ethylene glycol dimethyl ether and ethylene glycol diethyl ether.

The amount of the solvent is not particularly limited. The amount of the solvent is preferably 50 ml to 200 ml relative to 1.0 mol of 2-isopropenyl-5-methyl-4-hexen-1-ol (1), and is particularly preferably 50 ml to 100 ml relative to 1.0 mol of 2-isopropenyl-5-methyl-4-hexen-1-ol (1) from the viewpoint of cost efficiency and reactivity.

The transesterification is typically carried out under heating and is preferably carried out at a temperature equal to or higher than the boiling point of the alcohol formed as a by-product. For example, when methyl senecioate is used as the alkyl senecioate, the transesterification is carried out preferably at 65° C. to 140° C. under atmospheric pressure, and is carried out particularly preferably at 80° C. to 120° C. under atmospheric pressure from the viewpoint of reactivity and a small amount of impurity. When ethyl senecioate is used as the alkyl senecioate, the transesterification is carried out preferably at 80° C. to 160° C. under atmospheric pressure, and is carried out particularly preferably at 100° C. to 140° C. under atmospheric pressure from the viewpoint of reactivity and a small amount of impurity.

During the transesterification, the alcohol formed as a by-product as the reaction progresses is removed by distillation. In order to facilitate the removal of the alcohol formed as a by-product, the reaction can be carried out under reduced pressure.

The reaction mixture obtained by the transesterification can be purified by distillation in the same reactor or the same distillation apparatus as that used for the transesterification, preferably being subjected neither to reaction termination treatment nor to post-treatment for removing a substance that adversely affects the target compound, so as to obtain 2-isopropenyl-5-methyl-4-hexen-1-yl 3-methyl-2-butenoate as the target compound at high purity and high yield.

Typically, the purification by distillation is carried out under reduced pressure, and the target compound is distilled preferably at a boiling point of 60 to 150° C./0.013 KPa to 1.333 KPa.

In the method in accordance with the invention, decrease of the yield due to a by-product formed during the distillation is not observed unlike WO 2008/075468, and 2-isopropenyl-5-methyl-4-hexen-1-yl 3-methyl-2-butenoate as the target compound can be produced at a good yield. The content of 2-isopropenyl-5-methyl-4-hexen-1-yl 3-methyl-3-butenoate, which is an isomer contained by the 2-isopropenyl-5-methyl-4-hexen-1-yl 3-methyl-2-butenoate fraction, varies depending on distillation conditions when the target compound is isolated by the distillation, but can be suppressed to preferably 0.5% by weight or less, more preferably 0.3% by weight or less, even more preferably 0.15% by weight or less in the isolated fraction. The lower limit of the content of the isomer is preferably 0% by weight, that is, undetectable, but the isomer is typically present in an amount of more than 0% by weight.

The present invention will next be specifically explained with reference to Examples. However, it should not be construed that the present invention is limited to or by Examples.

EXAMPLES

Example 1

In a reactor equipped with a stirrer, a distillation column, a side-arm distillation head, a cooling condenser and a thermometer, 2-isopropenyl-5-methyl-4-hexen-l-ol (154.25 g: 1.0 mol), methyl senecioate (136.97 g: 1.2 mol) and titanium(IV) isopropoxide (2.84 g: 0.01 mol) were placed. The resulting mixture was heated at 100° C. Methanol formed as a by-product as the reaction progressed was distilled off through the side-arm distillation head. After the completion of the distillation of methanol, the pressure in the reactor is gradually reduced to 0.133 KPa, the temperature in the reactor was raised to 120° C., and excess methyl senecioate was distilled. Subsequent vacuum distillation provided 2-isopropenyl-5-methyl-4-hexen-1-yl 3-methyl-2-butenoate as the target compound (b.p. of 89-92° C/0.133 KPa, 223.59 g: 0.95 mol, yield of 94.6%, purity of 99.2%).

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.09% as a result of gas chromatography analysis.

The structure of the obtained 2-isopropenyl-5-methyl-4-hexen-1-yl 3-methyl-2-butenoate was identified by a $^1$H-nuclear magnetic resonance spectrum, a $^{13}$C-nuclear magnetic resonance spectrum, a mass spectrum and an IR spectrum. The isomer, 2-isopropenyl-5-methyl-4-hexen-1-yl 3-methyl-3-butenoate, was isolated by a precise preparative capillary gas chromatography system, and the structure was identified by a $^1$H-nuclear magnetic resonance spectrum, a mass spectrum and an IR spectrum.

<Spectral Data of 2-isopropenyl-5-methyl-4-hexen-1-yl 3-methyl-2-butenoate>

Nuclear magnetic resonance spectrum, $^1$H-NMR (500 MHz, CDCl$_3$): δ 1.59 (3H, s), 1.67 (3H, s), 1.70 (3H, s), 1.88 (3H, d), 2.00-2.25 (2H, m), 2.15 (3H, d), 2.41 (1H, tt), 4.06 (2H, td), 4.74 (1H, s), 4.82 (1H, s), 5.06 (1H, t) and 5.65 (1H, s).

$^{13}$C-NMR (126 MHz, CDCl$_3$): δ 17.79, 19.94, 20.17, 25.72, 27.34, 28.67, 46.14, 65.09, 112.23, 116.09, 121.73, 132.79, 145.08, 156.37 and 166.70.

Mass spectrum EI (70 eV): m/z 236 (M$^+$), 136 (M$^+$—C$_4$H$_7$CO$_2$H), 121, 107, 95, 83, 69, 55, 41 and 29.

Infrared absorption spectrum (liquid film): ν (cm$^{-1}$) 850, 891, 1006, 1077, 1145, 1226, 1269, 1347, 1377, 1447, 1650, 1719, 2915 and 2970.

<Spectral Data of 2-isopropenyl-5-methyl-4-hexen-1-yl 3-methyl-3-butenonate>

Nuclear magnetic resonance spectrum, $^1$H-NMR (500 MHz, CDCl$_3$): δ 1.60 (3H, s), 1.68 (3H, s), 1.69 (3H, s), 1.80 (3H, d), 2.10-2.29 (2H, m), 2.40 (1H, tt), 3.01 (2H, s), 4.07 (2H, td), 4.73 (1H, s), 4.83 (1H, s), 4.84 (1H, s), 4.90 (1H, s) and 5.06 (1H, t).

Mass spectrum EI (70 eV): m/z 236 (M$^+$), 136 (M$^+$—C$_4$H$_7$CO$_2$H), 121, 107, 93, 83, 81, 69, 55, 41 and 29.

Infrared absorption spectrum (liquid film): ν (cm$^{-1}$) 897, 1009, 1032, 1152, 1245, 1331, 1376, 1449, 1652, 1737, 2851, 2919, 2972 and 3078.

Example 2

The reaction was carried out in the same manner as in Example 1 except that the amount of titanium(IV) isopropoxide was 14.20 g (0.05 mol). As a result, 2-isopropenyl-5-methyl-4-hexen-1-yl 3-methyl-2-butenoate (b.p. of 90-93° C./0.133 KPa, 183.88 g: 0.78 mol, yield of 77.8%, purity of 98.9%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.11% as a result of gas chromatography analysis.

Example 3

The reaction was carried out in the same manner as in Example 1 except that ethyl senecioate (153.80 g: 1.2 mol) was used in place of methyl senecioate, and the reaction temperature of the transesterification was 120° C. As a result, 2-isopropenyl-5-methyl-4-hexen-1-yl 3-methyl-2-butenoate (b.p. of 93-94° C./0.133 KPa, 218.39 g: 0.92 mol, yield of 92.4%, purity of 98.4%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.10% as a result of gas chromatography analysis.

Example 4

The reaction was carried out in the same manner as in Example 1 except that the amount of methyl senecioate used was 228.28 g (2.0 mol). As a result, 2-isopropenyl-5-methyl-4-hexen-1-yl 3-methyl-2-butenoate (b.p. of 90-94° C./0.133 KPa, 219.81 g: 0.93 mol, yield of 93.0%, purity of 99.0%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.12% as a result of gas chromatography analysis.

Example 5

The reaction was carried out in the same manner as in Example 1 except that toluene (50.0 ml) was used as the solvent for the transesterification. As a result, 2-isopropenyl-5-methyl-4-hexen-1-yl 3-methyl-2-butenoate (b.p. of 87-90° C./0.133 KPa, 224.30 g: 0.95 mol, yield of 94.9%, purity of 99.1%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.10% as a result of gas chromatography analysis.

Example 6

The reaction was carried out in the same manner as in Example 1 except that dibutyltin oxide (2.48 g: 0.01 mol) was used in place of titanium(IV) isopropoxide. As a result, 2-isopropenyl-5-methyl-4-hexen-1-yl 3-methyl-2-butenoate (b.p. of 90-93° C./0.133 KPa, 213.19 g: 0.90 mol, yield of 90.2%, purity of 99.0%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.12% as a result of gas chromatography analysis.

Example 7

The reaction was carried out in the same manner as in Example 1 except that dibutyltin dichloride (3.04 g: 0.01 mol) was used in place of titanium(IV) isopropoxide. As a result, 2-isopropenyl-5-methyl-4-hexen-1-yl 3-methyl-2-butenoate (b.p. of 90-93° C./0.133 KPa, 207.52 g: 0.87 mol, yield of 87.8%, purity of 98.8%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.09% as a result of gas chromatography analysis.

Example 8

The reaction was carried out in the same manner as in Example 1 except that aluminum isopropoxide (2.04 g: 0.01 mol) was used in place of titanium(IV) isopropoxide. As a result, 2-isopropenyl-5-methyl-4-hexen-1-yl 3-methyl-2-butenoate (b.p. of 90-93° C./0.133 KPa, 210.59 g: 0.89 mol, yield of 89.1%, purity of 98.6%) was obtained as the target compound.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 0.10% as a result of gas chromatography analysis.

Comparative Example 1

In a reactor equipped with a stirrer, a cooling condenser and a thermometer, 2-isopropenyl-5-methyl-4-hexen-1-ol (154.25 g: 1.0 mol), triethylamine (122.44 g: 1.21 mol) and toluene (775.6 g) were placed. The resulting mixture was cooled at 5° C. Methanesulfonyl chloride (137.46 g: 1.20 mol) was added dropwise thereto over 2 hours, while keeping the reaction solution at 20° C. or lower. After the dropwise addition was over, the temperature of the reaction solution was increased to 25° C., and then the reaction solution was stirred for 1 hour. The reaction was stopped by addition of water (462.4 g) into the reaction solution, and the water phase was removed. The organic phase was washed with 5% by weight aqueous sodium hydrogen carbonate solution, followed by water (464.1 g). The organic phase was subjected to removal of solvent under reduced pressure, and then provided 2-isopropenyl-5-methyl-4-hexen-1-yl methanesulfonate (225.72 g: 0.98 mol, yield of 98.0%, purity of 97.8%).

In a reactor equipped with a stirrer, a cooling condenser and a thermometer, senecionic acid (111.13 g: 1.11 mol), potassium carbonate (105.04 g: 0.76 mol), tetrabutylammonium chloride (11.39 g: 0.04 mol), water (9.1 g) and toluene (765.7 g) were placed. The resulting mixture was stirred at 90 to 95° C. for 30 minutes. After the stirring, a solution of the above 2-isopropenyl-5-methyl-4-hexen-1-yl methanesulfonate (230.33 g: 1.0 mol) in toluene (797.1 g) was added dropwise thereto over 10 hours. After the dropwise addition was over, the resulting mixture was stirred at 90 to 95° C. for 6 hours. The reaction was stopped by addition of water (698.2 g) into the reaction solution, and the water phase was removed. The organic phase was washed with water (465.8 g). The organic phase was subjected to removal of solvent under reduced pressure, and then distilled under reduced pressure to obtain 2-isopropenyl-5-methyl-4-hexen-1-yl 3-methyl-2-butenoate (203.26 g: 0.86 mol, yield of 86.2%, purity of 95.5%) was obtained.

The content of 2-isopropenyl-5-methyl-4-hexen-1-yl 3-methyl-3-butenoate, which was an isomer contained by the 2-isopropenyl-5-methyl-4-hexen-1-yl 3-methyl-2-butenoate fraction, was 1.87% as a result of gas chromatography analysis.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. A method for producing 2-isoproponyl-5-methyl-4-hexen-1-yl 3-methyl-2-butenoate, comprising a step of transesterifying 2-isopropenyl-5-methyl-4-hexen-1-ol represented by Formula (1):

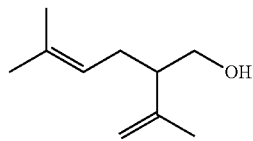
(1)

with alkyl senecioate represented by General Formula (2):

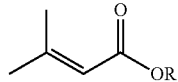
(2)

wherein R is a saturated or unsaturated linear alkyl group having 1 to 6 carbon atoms, in the presence of a catalyst, while distilling off an alcohol represented by General Formula (4):

ROH (4)

formed as a by-product, to obtain the 2-isopropenyl-5-methyl-4-hexen-1-yl 3-methyl-2-butenoate represented by Formula (3):

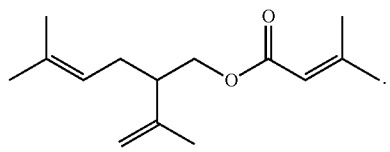
(3)

wherein the catalyst is a Lewis acid containing a titanium atom, a tin atom or an aluminum atom.

2. The method for producing 2-isopropenyl-5-methyl-4-hexen-1-yl 3-methyl-2-butenoate according to claim 1, wherein the catalyst is selected from the group consisting of titanium(IV) methoxide, titanitun(IV) ethoxide, titanium (IV) isopropoxide, dibutyhin dimethoxide, dibutyltin oxide, dibutyltin diehiorid, uminum methoxide, aluminum ethoxide, and aluminum isopropoxide.

* * * * *

UNITED STATES PATENT AND TRADEMARK OFFICE
CERTIFICATE OF CORRECTION

PATENT NO. : 9,738,587 B2
APPLICATION NO. : 14/950125
DATED : August 22, 2017
INVENTOR(S) : Yamashita et al.

It is certified that error appears in the above-identified patent and that said Letters Patent is hereby corrected as shown below:

In the Claims

Column 10, Claim 2, Lines 41-43: Please correct "titaitun(IV) ethoxide, titanium(IV) isopropoxide, dibutyhin dimethoxide, dibutyltin oxide, dibutyltin diehiorid, uminum methoxide" to read -- titanium(IV) ethoxide, titanium(IV) isopropoxide, dibutyltin dimethoxide, dibutyltin oxide, dibutyltin dichloride, aluminum methoxide --

Signed and Sealed this
Fifth Day of June, 2018

Andrei Iancu
*Director of the United States Patent and Trademark Office*